(12) United States Patent
Puhala et al.

(10) Patent No.: US 9,249,305 B2
(45) Date of Patent: Feb. 2, 2016

(54) SEQUESTERING POLYCYCLIC AROMATIC HYDROCARBONS IN ASPHALT

(71) Applicants: Aaron S. Puhala, Kent, OH (US); James W. Hoover, N. Canton, OH (US); Xiaofan Luo, Cleveland, OH (US)

(72) Inventors: Aaron S. Puhala, Kent, OH (US); James W. Hoover, N. Canton, OH (US); Xiaofan Luo, Cleveland, OH (US)

(73) Assignee: Flow Polymers, LLC, Cleveland, OH (US)

( * ) Notice: Subject to any disclaimer, the term of this patent is extended or adjusted under 35 U.S.C. 154(b) by 0 days.

(21) Appl. No.: 14/506,162

(22) Filed: Oct. 3, 2014

(65) Prior Publication Data

US 2015/0020711 A1 Jan. 22, 2015

Related U.S. Application Data

(62) Division of application No. 13/613,191, filed on Sep. 13, 2012, now Pat. No. 8,852,424.

(60) Provisional application No. 61/535,417, filed on Sep. 16, 2011.

(51) Int. Cl.

| | |
|---|---|
| *C08L 95/00* | (2006.01) |
| *C10C 3/00* | (2006.01) |
| *B27K 3/38* | (2006.01) |
| *C07C 15/20* | (2006.01) |
| *C08L 21/00* | (2006.01) |

(52) U.S. Cl.
CPC . *C08L 95/00* (2013.01); *B27K 3/38* (2013.01); *C07C 15/20* (2013.01); *C08L 21/00* (2013.01); *C10C 3/00* (2013.01)

(58) Field of Classification Search
CPC ...................................... C08L 95/00
USPC .................................... 208/39–45
See application file for complete search history.

(56) References Cited

U.S. PATENT DOCUMENTS

| | | | |
|---|---|---|---|
| 4,100,059 A | 7/1978 | Jinno | 209/3 |
| 4,977,871 A | 12/1990 | Brownawell et al. | 123/196 A |
| 5,069,799 A | 12/1991 | Brownawell | 210/749 |
| 5,225,081 A | 7/1993 | Brownawell | 210/690 |
| 5,374,350 A * | 12/1994 | Heck et al. | 208/143 |
| 5,614,459 A * | 3/1997 | Mondragon et al. | 502/417 |
| 5,656,041 A | 8/1997 | Hylton | 44/607 |
| 7,566,394 B2 | 7/2009 | Koseoglu | 208/309 |
| 7,811,373 B2 | 10/2010 | Partanen et al. | 106/284.01 |
| 8,012,242 B2 * | 9/2011 | Kozliak et al. | 95/141 |
| 8,246,814 B2 | 8/2012 | Koseoglu | 208/250 |
| 8,444,761 B2 | 5/2013 | Al-Mehthel et al. | 106/281.1 |
| 8,759,253 B2 * | 6/2014 | De Leede et al. | 502/424 |
| 2006/0183812 A1 * | 8/2006 | Miller et al. | 523/102 |
| 2008/0271639 A1 | 11/2008 | Partanen et al. | 106/294.01 |
| 2009/0283012 A1 | 11/2009 | Partanen et al. | 106/284.01 |
| 2009/0288991 A1 | 11/2009 | Partanen et al. | 208/127 |
| 2009/0301931 A1 | 12/2009 | Koseoglu et al. | 208/22 |
| 2013/0241094 A1 * | 9/2013 | Yu et al. | 264/15 |
| 2014/0305840 A1 * | 10/2014 | Koseoglu et al. | 208/22 |

* cited by examiner

*Primary Examiner* — Ellen McAvoy
(74) *Attorney, Agent, or Firm* — Alvin T. Rockhill

(57) ABSTRACT

This invention is based upon the discovery that activated carbon can be used to sequester polycyclic aromatic hydrocarbons that may be present in asphalt and creosote compositions. The treatment of asphalt and creosote compositions with activated carbon accordingly reduces the level of free polycyclic aromatic hydrocarbons in such compositions by sequestering them therein or removing them from the composition. After being sequestered the polycyclic aromatic hydrocarbons remain trapped in the asphalt or creosote composition, and are not available to the environment during normal processing into useful industrial products. This sequestration reduces the risk of exposing humans and the environment to the polycyclic aromatic hydrocarbons which would otherwise be free to migrate from the asphalt or creosote product during manufacturing and the service life of the product. In other words, the polycyclic aromatic hydrocarbons are absorbed onto the activated carbon and are not available for bioaccumulation from the environment.

20 Claims, No Drawings

SEQUESTERING POLYCYCLIC AROMATIC HYDROCARBONS IN ASPHALT

This is a divisional application of U.S. patent application Ser. No. 13/613,191 filed on Sep. 13, 2012 which claims the benefit of U.S. Provisional Patent Application Ser. No. 61/535,417, filed on Sep. 16, 2011. The teachings of U.S. patent application Ser. No. 13/613,191 and U.S. Provisional Patent Application Ser. No. 61/535,417 are incorporated herein by reference in their entirety.

BACKGROUND OF THE INVENTION

Polycyclic aromatic hydrocarbons are solid materials with low volatility. Polycyclic aromatic hydrocarbons are fat soluble and are generally believed to be carcinogenic, mutagenic and teratogenic (cause deformities). Several hundred polycyclic aromatic hydrocarbons have been identified in creosote, the combustion product of petrochemicals and wood, and in asphalt. Some common examples of polycyclic aromatic hydrocarbons include: naphthalene, methylnaphthalenes, acenaphthalene, acenaphthene, fluorene, phenanthrene, anthracene, fluoranthrene, pyrene, benzo(a)anthracene, chrysene, benzo(b)fluoranthene, benzo(j)fluoranthene, benzo(k)fluoranthene, benzo(e)pyrene, benzo(a)pyrene, perylene, indeno[123-cd]pyrene, dibenzo(a,h)anthracene, and benzo(ghi)perylene.

| Structure | |
|---|---|
| Benzo(a)pyrene | 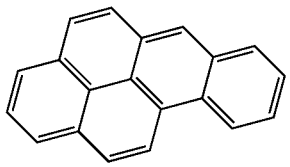 [SMILES: c1ccc2c(c1)cc1ccc3cccc4ccc2c1c34] |
| Benzo(e)pyrene | 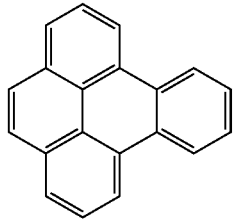 [SMILES: c1ccc2c(c1)c1cccc3ccc4cccc2c4c31] |
| Benzo(a)anthracene | 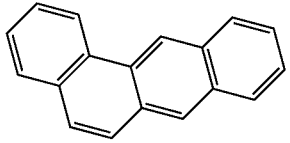 [SMILES: c1ccc2cc3c(ccc4ccccc43)cc2c1] |
| Chrysene | 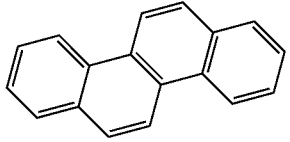 [SMILES: c1ccc2c(c1)ccc1c3ccccc3ccc21] |
| Benzo(b)fluoranthene | 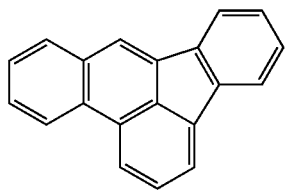 [SMILES: c1ccc2c(c1)-c1cccc3c1c-2cc1ccccc13] |
| Benzo(j)fluoranthene | 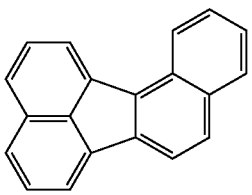 [SMILES: c1ccc2c3c(ccc2c1)-c1cccc2cccc-3c12] |
| Benzo(k)fluoranthene | 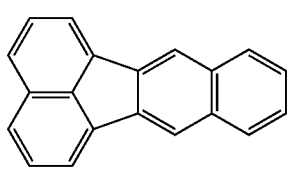 [SMILES: c1ccc2cc3c(cc2c1)-c1cccc2cccc-3c12] |
| Dibenzo(a,h)anthracene | 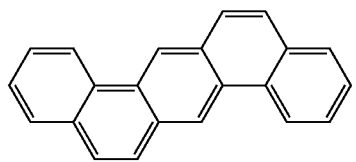 [SMILES: c1ccc2c(c1)ccc1cc3c(ccc4ccccc43)cc12] |

Unfortunately, polycyclic aromatic hydrocarbons have a low degradation rate and tend to prevail in creosote and asphalt over extender periods of time. Since polycyclic aromatic hydrocarbons present potential health concerns, it is desirable to reduce the level of human and environmental exposure to such compounds by removing them from or sequestering them in materials where they are present, such as asphalt, creosote, and rubber or plastic products. This is a particularly important objective in cases where products made with materials containing polycyclic aromatic hydrocarbons come into close proximity to humans and/or the environment during manufacturing or during the service life of the product. For instance, recent European legislation requires that extender oils utilized in manufacturing tires for sale in Europe contain no more than 1 mg/kg of benzo(a)pyrene. Accordingly, the amount of polycyclic aromatic hydrocarbons present in a manufactured product can, in some cases, be limited by reducing the quantity of polycyclic aromatic hydrocarbon-containing material incorporated into the product during manufacturing. However, elimination of all PAH or reduction of PAH content to very low levels may not be possible in cases where polycyclic aromatic hydrocarbons are inherently present in the material, such as in asphalt and creosote containing products.

The use of coal-tar creosote on a commercial scale began the early part of the 19$^{th}$ Century after the pressure treatment of wood with coal-tar creosote was developed by John Bethell. This process was originally known as the "Bethell process" and is generally referred to today as the fuel-cell process. In any case, it involves sealing wood in a pressure chamber and applying a vacuum to remove air and moisture from the wood cells. The wood is then pressure treated to impregnate it with the creosote. After this pressure treatment vacuum is normally applied to remove excess creosote from the wood being treated.

In the early 20$^{th}$ century the empty-cell process for treating wood with creosote was developed. This process involves compressing air inside the wood so that the creosote preservative can only coat the inner cell walls rather than saturating the interior cell voids. The empty-cell process is a less effective than the fuel-cell process, but is used because it requires less of the creosoting preservative to treat the same quantity of wood. In any case, important uses for creosote treated wood include railroad ties or sleepers, utility poles (telephone poles and power line poles), ground pilings, marine pilings, and fence posts. However, creosote treated wood can be advantageously employed in a wide variety of applications where toxicity to fungi, insects, and marine borers is desired. Creosote also serves beneficially in many applications as a natural water repellant.

U.S. Pat. No. 5,656,041 discloses a process for detoxifying a coal-tar deposit comprising: adding at a mixing station effective amounts of carbon and a calcium oxide containing substance to at least a portion of said coal-tar deposit, thereby forming a reaction mixture; and mixing said reaction mixture at a temperature of from about 70° F. to about 130° F. for a time sufficient to detoxify the reaction mixture and convert it into a non-hazardous reaction product.

U.S. Pat. No. 4,977,871 discloses a system for the selective removal of polynuclear aromatic hydrocarbons containing 3 or more aromatic rings from lubricating oil used to lubricate the engine of a motor vehicle which comprises activated carbon positioned within the lubricating system and through which the lubricating oil circulates, said activated carbon being selective to removing polynuclear aromatic hydrocarbons containing 3 or more aromatic rings from the lubricating oil.

U.S. Pat. No. 5,069,799 and U.S. Pat. No. 5,225,081 relate to a method for removing polynuclear aromatics from a used lubricating oil which comprises passing the lubricating oil through a filter system containing a hollow solid composite comprising a thermoplastic binder and activated carbon, wherein the composite is formed by the steps comprising (a) providing a quantity of the thermoplastic binder in the form of particles having diameters between about 0.1 and about 250 micrometers; (b) providing a quantity of activated carbon having a softening temperature substantially greater than the softening temperature of the thermoplastic binder, the activated carbon being in the form of particles having diameters between about 0.1 and about 3,000 micrometers; (c) combining the particles from (a) and (b) to form a substantially uniform mixture wherein from about 2 to about 25 weight percent of the thermoplastic binder and about 40 to about 75 weight percent of the activated carbon are present in the mixture; (d) extruding the substantially uniform mixture of (c) into a die; (e) heating the substantially uniform mixture from (d) to a temperature substantially above the softening temperature of the thermoplastic binder but to a temperature less than the softening temperature of the activated carbon; (f) applying sufficient back pressure, from outside the die, to the heated mixture from (e) within the die to convert the heated mixture into a substantially homogeneous composite; (g) rapidly cooling the composite from (f) to a temperature below the softening point of the thermoplastic binder to produce a cooled composite; and (h) extruding the cooled composite from the die as an extruded hollow solid composite.

U.S. Pat. No. 4,100,059 discloses an asphalt recycling method comprising the steps of: (a) introducing (1) asphalt waste and (2) activated terra alba, activated carbon or a mixture thereof into a tank of water; (b) jetting steam into said water to heat said water to a temperature sufficient to soften the asphalt waste; and (c) mechanically subdividing the asphalt waste while immersed in the heated water into aggregate grains, each aggregate having a surface coated with a thin asphalt film.

United States Patent Publication No. 2009/0301931 reveals a cost-effective solution is provided for eliminating refinery process waste, including spent catalytic and non-catalytic adsorbent materials, as well as adsorbate process reject materials derived from desorption, while minimizing conventional waste handling demands. The asphalt composition of United States Patent Publication No. 2009/0301931 includes asphalt and spent adsorbent material from a solvent deasphalting unit. This asphalt can comprise asphaltic material obtained from a solvent deasphalting unit, and spent adsorbent material in the asphalt composition was previously utilized in the solvent deasphalting unit. The asphalt composition of United States Patent Publication No. 2009/0301931 can also include process reject materials.

United States Patent Publication No. 2009/0283012 discloses a process for manufacturing a foamed asphalt composition, said process comprising: (a) comminuting spent, unregenerated activated carbon to particles whose longest dimension is a maximum of about 250 microns; (b) heating said comminuted activated carbon to an elevated temperature of from about 100° C. to about 300° C. to remove therefrom volatile species having boiling points below said elevated temperature; (c) following removal of said volatile species therefrom, exposing said activated carbon to moisture to cause said activated carbon to absorb said moisture to a level of from about 1% to about 25% by weight; and (d) combining said activated carbon with a liquid asphalt composition at a temperature of at least about 120° C. to cause said liquid asphalt composition to foam.

SUMMARY OF THE INVENTION

This invention is based in part upon the discovery that activated carbon can be used to sequester polycyclic aromatic hydrocarbons that may be present in asphalt and creosote compositions. The treatment of asphalt and creosote compositions with activated carbon accordingly reduces the level of free polycyclic aromatic hydrocarbons in such compositions by sequestering them therein. For purposes of this invention "free" polycyclic aromatic hydrocarbons are not sequestered on or bound to any constituents of the asphalt composition and are according capable of migrating throughout the asphalt composition and ultimately escaping into the environment around the asphalt composition. In any case, after being sequestered the polycyclic aromatic hydrocarbons remain trapped in the asphalt or creosote composition during normal processing into useful industrial products and throughout the service life of such products. This reduces to risk of human and environmental exposure to the polycyclic aromatic hydrocarbons which would otherwise be free to migrate from the asphalt or creosote product during manufacturing and the service life of the product. In other words, the polycyclic aromatic hydrocarbons are absorbed onto the activated carbon and are not available for bioaccumulation from the environment.

The subject invention more specifically discloses a method for sequestering free polycyclic aromatic hydrocarbons from an asphalt composition comprising: (1) heating the asphalt composition to an elevated temperature, (2) mixing an activated carbon throughout the asphalt composition, and (3) maintaining the asphalt composition containing the activated carbon at the elevated temperature for a period of time which is sufficient for the activated carbon to sequester the free polycyclic aromatic hydrocarbons in the asphalt composition, wherein the elevated temperature is above the softening point of the asphalt.

The present invention also reveals a method for removing free polycylic aromatic hydrocarbons from asphalt compositions which comprises sequestering the free polycylic aromatic hydrocarbons in the asphalt composition and which further comprises removing the activated carbon having the polycylic aromatic hydrocarbons sequestered thereon from the asphalt composition.

The subject invention further discloses an asphalt composition having a low level of free polycyclic aromatic hydrocarbons which is comprised of an asphalt and activated carbon having polycylic aromatic hydrocarbons sequestered thereon, wherein the level of free benzo(a)pyrene is less than 1 ppm, and preferably less than 0.5 ppm.

The present invention also reveals a creosote composition having a reduced level of free polycyclic aromatic hydrocarbons which is comprised of creosote and activated carbon having polycylic aromatic hydrocarbons sequestered thereon. In such creosote compositions the level of free benzo(a)pyrene is less than 500 ppm, preferably less than 100 ppm, and most preferably less than 50 ppm.

The subject invention also discloses a process for preserving a wood product to make it more resistant to decay, fungi, and insects, said process comprising coating at least a portion of the surface of the wood product with a creosote composition having a reduced level of free polycyclic aromatic hydrocarbons which is comprised of creosote and activated carbon having polycylic aromatic hydrocarbons sequestered thereon. To make the preservation more effective zinc chloride is commonly included in the creosote composition. The creosote composition can be simply sprayed, rolled or brushed onto the wood product or it can be applied via the fuel-cell process (the Bethell process) or the empty-cell process. For optimal results it is typically preferred for the wood product to be pressure treated with the creosote composition via the fuel-cell process under which wood product is subjected to a vacuum prior to being treated with the creosote composition and wherein the creosote composition is applied to the wood product under pressure. Excess creosote composition can optionally be removed from the wood product by the application of vacuum in a subsequent processing step.

DETAILED DESCRIPTION OF THE INVENTION

Asphalt offers outstanding binding and waterproofing characteristics. These physical attributes of asphalt have led to its widespread utilization in paving, roofing, and waterproofing applications. For instance, asphalt is used in manufacturing roofing shingles because it has the ability to bind sand, aggregate, and fillers to the roofing shingle while simultaneously providing excellent water barrier characteristics. The ability of asphalt to bind aggregate to produce paving surfaces that can be relatively easily applied and which have good durability is also well known. In all of these applications humans and the environment are potentially exposed to polycyclic aromatic hydrocarbons that migrate from the asphalt. This problem is of particular concern in applications where the asphalt is manufactured into articles, such as roofing shingles, in a closed environment, such as in a factory building. However, it can also be of concern in outdoor applications, such as in paving roadways, where workers may be exposed to hot asphalt over extended periods of time. Another concern is the exposure of children to polycyclic aromatic hydrocarbons which migrate from playground surfaces which are paved with asphalt.

The method of this invention is applicable to virtually any asphalt that contains free polycyclic aromatic hydrocarbons. For instance, it is applicable to naturally occurring asphalts that have been used in various applications for hundreds of years. It can also be used in treating asphalt recovered from the refining of petroleum which is used in most industrial applications around the world today. In any case, such asphalt, or asphalt flux, is essentially the residue that remains after gasoline, kerosene, diesel fuel, jet fuel, and other hydrocarbon fractions have been removed during the refining of crude oil. In other words, asphalt, or asphalt flux, or asphalt pitch, is the last cut from the crude oil refining process.

To meet performance standards and product specifications, asphalt that is recovered from refining operations is normally treated or processed to attain desired physical characteristics and to attain uniformity. For instance, asphalt that is employed in manufacturing roofing products has to be treated to meet the special requirements demanded in roofing applications. More specifically, in the roofing industry it is important to prevent asphaltic materials from flowing under conditions of high temperature such as those encountered during hot summers. In other words, the asphaltic materials used in roofing products should maintain a certain level of stiffness (hardness) at high temperatures. This increased level of stiffness is characterized by a reduced penetration, an increased viscosity, and an increased softening point. To attain the required level of stiffness and increased softening point that is demanded in roofing applications the asphalt is typically treated by an air blowing process. In such air blowing techniques, air is blown through the asphalt for a period of about 2 to about 8 hours while it is maintained at an elevated temperature which is typically within the range of 400° F. (204° C.) to 550° F. (288° C.). The air blowing process results in the stiffness and softening point of the asphalt being significantly increased. This is highly desirable because ASTM D 3462-96 (Standard Specification for Asphalt Shingles Made from Glass Felt and Surfaced with Mineral Granules) requires roofing asphalt to have a softening point which is within the range of 190° F. (88° C.) to 235° F. (113° C.) and for the asphalt to exhibit a penetration at 77° F. (25° C.) of above 15 dmm (1 dmm=0.1 mm). In fact, it is typically desirable for asphalt used in roofing applications to have a penetration which is within the range of 15 dmm to 35 dmm in addition to a softening point which is within the range of 185° F. (85° C.) to 235° F. (113° C.).

Penetration values can be determined at room temperature or at an elevated temperature. Unless stated otherwise, penetration values are determined at room temperature. For purposes of this invention, asphalt softening points are measured following ASTM D 36-95 "Standard Test Method for Softening Point of Bitumen (Ring- and Ball Apparatus)" and asphalt penetrations are measured following ASTM D 5-97 "Standard Test Method for Penetration of Bituminous Materials".

Air blowing has been used to increase the softening point and stiffness of asphalt since the early part of the twentieth century. For example, U.S. Pat. No. 2,179,208 describes a process wherein asphalt is air blown at a temperature of 300° F. (149° C.) to 500° F. (260° C.) in the absence of a catalyst for a period of 1 to 30 hours after which time a polymerization catalyst is added for an additional treatment period of 20 to 300 minutes at a temperature of 225° F. (107° C.) to 450° F. (232° C.). Over the years a wide variety of chemical agents have been used as air blowing catalysts. For instance, ferric chloride (FeCl$_3$) as described in U.S. Pat. No. 1,782,186, phosphorous pentoxide (P$_2$O$_5$) as described in U.S. Pat. No. 2,450,756, aluminum chloride (AlCl$_3$) as described in U.S. Pat. No. 2,200,914, boric acid as described in U.S. Pat. No. 2,375,117, ferrous chloride (FeCl$_2$), phosphoric acid (H$_3$PO$_4$) as described in U.S. Pat. No. 4,338,137, copper sulfate (CuSO$_4$), zinc chloride (ZnCl$_2$), phosphorous sesquesulfide (P$_{4}$S$_3$), phosphorous pentasulfide (P$_2$S$_5$), and phytic acid (C$_6$H$_6$O$_6$(H$_2$PO$_3$)$_6$) as described in U.S. Pat. No. 4,584,023 have all been identified as being useful as air blowing catalysts.

The technique of this invention for sequestering free polycyclic aromatic hydrocarbons in asphalt compositions can be practiced by simply dispersing activated carbon throughout the asphalt composition. To attain good mixing the asphalt composition will typically be heated to a temperature which is above its softening point. Normally, the asphalt will be heated to a temperature of at least about 40° C. to facilitate mixing and to attain a homogeneous dispersion of the activated carbon throughout the asphalt composition. However, the temperature utilized for the mixing will normally be no more than about 315° C. to minimize thermal degradation. The elevated temperature at which the activated carbon is mixed into the asphalt will typically be within the range of about 50° C. to about 280° C. and will more typically be within the range of 80° C. to 250° C.

The activated carbon can be dispersed into the asphalt utilizing any type of equipment that will provide the requisite degree of mixing to attain a relatively homogeneous mixture of the activated carbon throughout the asphalt. For instance, this mixing can be carried out in a mechanical blade mixer, a rotating drum mixer, or by passing it through an in-line static mixer. In one embodiment of this invention, the activated carbon can be added to the asphalt in the blow still utilized in air blowing industrial asphalt to the desired softening points and penetration values. In any case, the activated carbon can be added to and mixed throughout the asphalt continuously, semi-continuously, or in individual batches, depending upon the equipment available. Normally, the asphalt will be maintained at the desired elevated temperature throughout the mixing procedure and for a period of time which is adequate for the activated carbon to sequester the free polycyclic aromatic hydrocarbons present in the asphalt being treated. During this time period the asphalt will typically be maintained at the elevated temperature which is within the range of about 40° C. to 315° C. to allow for the free polycyclic aromatic hydrocarbons present in the asphalt composition to be sequestered by the activated carbon. Normally this will be accomplished over a period of about 2 hours to about 12 hours and is commonly done over a period of about 4 hours to about 8 hours. In one embodiment of this invention the activated carbon is added to the asphalt prior to or during the air blowing process utilized to modify the asphalt to a desired softening point and penetration value.

The amount of activated carbon added to the asphalt composition will typically be within the range of about 0.2 weight percent to about 20 weight percent, based upon the weight of the asphalt. In most cases the activated carbon will be mixed throughout the asphalt composition at a level which is within the range of about 0.5 weight percent to about 15 weight percent. Preferably, the activated carbon is mixed throughout the asphalt composition at a level which is within the range of 1.0 weight percent to about 5 weight percent.

The activated carbon that can be utilized in the practice of this invention is also sometimes referred to as activated charcoal, activated coal or carbo activatus. In any case, it is a form of carbon that has been processed to make it extremely porous which allows for it to have a very large surface area available for adsorption or chemical reactions. By virtue of its high degree of microporosity, just 1 gram of activated carbon has a surface area in excess of 500 m$^2$, as determined by nitrogen gas adsorption. The activated carbon used to sequester free polycyclic aromatic hydrocarbons is typically in the form of a powder, granules, extruded cylinders, or beads. Powdered activated carbon (PAC) typically has a particle size of less than 1.0 mm with an average diameter between 0.15 mm and 0.25 mm. It accordingly presents a large surface to volume ratio. Powdered activated carbon is generally comprised of crushed or ground carbon particles, 95-100% of which will pass through a designated mesh sieve or sieve. Granular activated carbon is defined as the activated carbon being retained on a 50-mesh sieve (0.297 mm) and PAC material as finer material, while ASTM classifies particle sizes corresponding to an 80-mesh sieve (0.177 mm) and smaller as powdered activated carbon.

Granular activated carbon (GAC) has a relatively larger particle size compared to powdered activated carbon and consequently, presents a smaller external surface. Granulated carbons are widely used for water treatment, deodorization and separation of components of flow systems. Granular activated carbon can be either in granular form or extruded. Granular activated carbon is designated by sizes such as 8×20, 20×40, or 8×30 for liquid phase applications and 4×6, 4×8 or 4×10 for vapor phase applications. A 20×40 carbon is made of particles that will pass through a U.S. Standard Mesh Size No. 20 sieve (0.84 mm), generally specified as 85% passing, but be retained on a U.S. Standard Mesh Size No. 40 sieve (0.42 mm), generally specified as 95% retained. AWWA (1992) B604 uses the 50-mesh sieve (0.297 mm) as the minimum granular activated carbon size. Extruded activated carbon (EAC) combines powdered activated carbon with a binder, which are fused together and extruded into a cylindrical shaped activated carbon block with diameters from 0.8 mm to 130 mm. Extruded activated carbon is widely used for gas phase applications because of their low pressure drop, high mechanical strength, and low dust content. Bead activated carbon (BAC) is made from petroleum pitch and supplied in diameters from approximately 0.35 mm to 0.80 mm. It is similar to extruded activated carbon in that it provides low pressure drop, high mechanical strength and low dust content, but with a smaller grain size. Its spherical shape makes it preferred for fluidized bed applications such as water filtration. The activated carbon can also be encapsulated in a polymeric binder, wherein the polymeric binder is permeable to the polycylic aromatic hydrocarbons. In such cases the polymeric binder should maintains its structural integrity throughout said process.

In one embodiment of this invention, polycyclic aromatic hydrocarbons are removed from the asphalt being treated. This is accomplished by first sequestering the polycyclic aromatic hydrocarbons on activated carbon as described heretofore and then removing the activated carbon having the polycyclic aromatic hydrocarbons sequestered on its surface from the asphalt. This is typically done by filtering the activated carbon from the asphalt after it has absorbed the polycyclic aromatic hydrocarbons in the asphalt composition. This filtration step is normally conducted at a temperature which is above the softening point of the asphalt. It is generally convenient to conduct this filtration step at the elevated temperature at which the asphalt is held while the polycyclic aromatic hydrocarbons are being sequestered. It is also conceived to perform the filtration step after first dispersing the asphalt composition containing the activated carbon with polycyclic aromatic hydrocarbons sequestered thereon into an oil or solvent in cases where an asphalt modified oil or solvent-cut asphalt is desired. In cases where the activated carbon having the polycyclic aromatic hydrocarbons sequestered thereon is removed from the asphalt it is normally preferable for the activated carbon to be granular activated carbon, extruded activated carbon, bead activated carbon, or for the activated carbon to be encapsulated in a polymeric binder to facilitate its removal from the asphalt.

The asphalt composition made by practicing the method of this invention typically has a low level of free polycylic aromatic hydrocarbons with the level of free benzo(a)pyrene being less than 1 ppm. In cases of industrial asphalt the asphalt composition will have a softening point which is within the range of 50° C. to 200° C. and a penetration value of less than 15 dmm. Such asphalt compositions will normally have a level of free benzo(a)pyrene which is less than 0.5 ppm and which is preferably less than 0.2 ppm.

EXAMPLE 1

Activated carbon was added to industrial oxidized asphalt having a ring and ball (R&B) softening point of 100° C. The asphalt was heated to a temperature of 450° F.-470° F. (232° C.-243° C.) with continuous stifling under a nitrogen purge. Activated carbon was added and the blend was stirred for 240 minutes at 450-470° F. (232° C.-243° C.) under a continuing nitrogen purge. During the stirring, samples were taken at time intervals of 0 minutes, 5 minutes, 30 minutes, 60 minutes, 120 minutes, and 240 minutes and tested for free Benzo(a)pyrene.

| Formulations and Properties | | | | | | |
|---|---|---|---|---|---|---|
| | 1 | 2 | 3 | 4 | 5 | 6 |
| Oxidized Asphalt | 100 | 90 | 90 | 90 | 90 | 90 |
| Activated Carbon | 0 | 10 | 10 | 10 | 10 | 10 |
| Mixing Time (min) | 0 | 5 | 30 | 60 | 120 | 240 |
| Free Benzo(a)Pyrene | 0.58 | 0.39 | 0.38 | 0.26 | 0.18 | 0.14 |

* Activated Carbon, WPH, available from Calgon Carbon.

EXAMPLE 2

Activated carbon was added at various levels to industrial O-PEN asphalt having a R&B softening point of 95° C. The asphalt was heated to a temperature of 450-470° F. (232° C.-243° C.) with continuous stifling under nitrogen purge. Activated carbon was added and the blend was stirred for four hours at 450-470° F. (232° C.-243° C.) under a continuing nitrogen purge. After four hours the mixture was cooled and tested for free Benzo(a)pyrene.

| Formulations and Properties | | | | |
|---|---|---|---|---|
| | 1 | 2 | 3 | 4 |
| O-PEN Asphalt | 100 | 95 | 90 | 85 |
| Activated Carbon | 0 | 5 | 10 | 15 |
| Free Benzo(a)Pyrene | 1.5 | 0.73 | 0.28 | 0.04 |

* Activated Carbon, WPH, available from Calgon Carbon.

EXAMPLE 3

Activated carbon was added to industrial O-PEN asphalt having a R&B softening point of 74° C. The asphalt was heated to a temperature of 450-470° F. (232° C.-243° C.) with continuous stirring under nitrogen purge. Activated carbon was added and the blend was stirred for four hours at 450-470° F. (232° C.-243° C.) under nitrogen purge. After four hours the mixture was filtered to remove the residual activated carbon, cooled and tested for free Benzo(a)pyrene.

| Formulations and Properties | | |
|---|---|---|
| | 1 | 2 |
| O-PEN Asphalt | 100 | 90 |
| Activated Carbon | 0 | 10 |
| Free Benzo(a)Pyrene | 4.41 | 3.08 |

* Activated Carbon Carbsorb 30, available from Calgon Carbon.

Description of "Free Benzo(a)pyrene"

Free Benzo(a)pyrene was determined in Examples 1-3 by Southwest Research Institute (SwRI) using a GC/MS (gas chromatograph/mass spectrometer) with isotope dilution. The method was presented at IRC (international rubber conference) 2008, in Kuala Lumpur, Malaysia, IRC 2012 on Jeju Island, Korea, and German Rubber Conference 2012, in Nurnberg, Germany. The method calls for spiking of deuterated PAH internal standard mixture (IS, 25 uL at 10 ng/uL each) at the beginning of the sample preparation/cleanup process.

In this procedure, an aliquot amount of sample (between 200 mg and 220 mg) was weighed, dissolved in 5 mL of a polar solvent in a 1-dram vial, and then transferred into a 50 mL volumetric flask. The volumetric flask was then filled to the 50 mL mark with a non-polar solvent and mixed well.

One 5.0 ml aliquot of the sample solution was taken out of 50 mL flask, then put into a 6-dram vials. The solution was spiked with 25 uL of PAH IS mix with each of the eighteen deuterated PAH IS at 10 ng/uL. Each sample was then treated with SwRI's proprietary oil sample extraction/cleanup procedures which include two liquid-liquid partitions and one adsorption chromatography. These proprietary sample extraction/cleanup procedures effectively eliminate most saturated hydrocarbons and at the same time preserve most PAHs. The final sample extract was concentrated down to 1.0 mL and analyzed by a GC/MS in selected ion monitoring (SIM) mode.

While certain representative embodiments and details have been shown for the purpose of illustrating the subject invention, it will be apparent to those skilled in this art that various changes and modifications can be made therein without departing from the scope of the subject invention.

What is claimed is:

1. An asphalt composition having a low level of free polycylic aromatic hydrocarbons which is comprised of an asphalt and activated carbon having polycylic aromatic hydrocarbons sequestered thereon, wherein the asphalt composition has a softening point which is within the range of 50° C. to 200° C., wherein the asphalt composition has a penetration value of less than 15 dmm, wherein the free polycyclic aromatic hydrocarbons include benzo(a)pyrene, benzo(e)pyrene, benzo(a)anthracene, chrysene, benzo(b)fluoranthene, benzo(j) fluoranthene, benzo(k)fluoranthene, and dibenzo(a,h)anthracene, and wherein the level of free benzo(a)pyrene is less than 1 ppm.

2. The asphalt composition as specified in claim 1 wherein the level of free benzo(a)pyrene is less than 0.5 ppm.

3. The asphalt composition as specified in claim 1 wherein the level of free benzo(a)pyrene is less than 0.2 ppm.

4. The asphalt composition as specified in claim 1 wherein the activated carbon is present in the asphalt composition at a level which is within the range of about 0.2 weight percent to about 20 weight percent.

5. The asphalt composition as specified in claim 1 wherein the activated carbon is present in the asphalt composition at a level which is within the range of about 0.5 weight percent to about 15 weight percent.

6. The asphalt composition as specified in claim 1 wherein the activated carbon is present in the asphalt composition at a level which is within the range of about 1 weight percent to about 5 weight percent.

7. The asphalt composition as specified in claim 1 wherein the activated carbon has a surface area in excess of 500 $m^2/g$, as determined by nitrogen gas absorption.

8. The asphalt composition as specified in claim 1 wherein the activated carbon is a powdered activated carbon having an average diameter which is within the range of 0.15 mm to 0.25 mm.

9. The asphalt composition as specified in claim 1 wherein the asphalt is for paving applications.

10. The asphalt composition as specified in claim 1 wherein the asphalt is for roofing applications.

11. The asphalt composition as specified in claim 1 wherein the asphalt is for waterproofing applications.

12. A rubber composition which is comprised of at least one rubbery polymer and the asphalt composition specified in claim 1.

13. A rubber article comprising the rubber composition of claim 12.

14. A modified plastic composition which is comprised of at least one thermoplastic resin and from about 1 weight percent to about 10 weight percent of the asphalt composition specified in claim 1.

15. A plastic article comprising the modified plastic composition of claim 14.

16. A creosote composition having a reduced level of free polycylic aromatic hydrocarbons which is comprised of creosote and activated carbon having polycyclic aromatic hydrocarbons sequestered thereon, wherein the free polycyclic aromatic hydrocarbons include benzo(a)pyrene, benzo(e)pyrene, benzo(a)anthracene, chrysene, benzo(b)fluoranthene, benzo(j)fluoranthene, benzo(k)fluoranthene, and dibenzo(a,h)anthracene, and wherein the level of free benzo(a)pyrene is less than 500 ppm.

17. A process for preserving a wood product to make it more resistant to decay, fungi, and insects, said process comprising coating at least a portion of the surface of the wood product with the creosote composition of claim 16.

18. The creosote composition as specified in claim 16 wherein the level of free benzo(a)pyrene is less than 100 ppm.

19. The creosote composition as specified in claim 16 wherein the level of free benzo(a)pyrene is less than 50 ppm.

20. An asphalt composition having a low level of free polycylic aromatic hydrocarbons which is comprised of an asphalt and activated carbon having polycylic aromatic hydrocarbons sequestered thereon, wherein the asphalt has a penetration value of 0 dmm, and wherein the free polycyclic aromatic hydrocarbons include benzo(a)pyrene, benzo(e)pyrene, benzo(a)anthracene, chrysene, benzo(b)fluoranthene, benzo(j)fluoranthene, benzo(k)fluoranthene, and dibenzo(a,h)anthracene, and wherein the level of free benzo(a)pyrene is less than 1 ppm.

* * * * *